United States Patent [19]

Morgenstern

[11] Patent Number: 4,884,578
[45] Date of Patent: Dec. 5, 1989

[54] APPARATUS FOR MONITORING RESPIRATION AND CARDIAC ACTIVITY

[76] Inventor: Jurgen Morgenstern, Im Heidewinkel 33, 4000 Dusseldorf, Fed. Rep. of Germany

[21] Appl. No.: 230,690

[22] Filed: Aug. 10, 1988

Related U.S. Application Data

[62] Division of Ser. No. 917,429, Oct. 10, 1986, abandoned.

[30] Foreign Application Priority Data

Oct. 12, 1985 [DE] Fed. Rep. of Germany ....... 3536491

[51] Int. Cl.$^4$ .............................................. A61B 5/02
[52] U.S. Cl. .................................... 128/670; 128/714; 128/721
[58] Field of Search ............... 128/670, 671, 714, 721, 128/722, 774, 897

[56] References Cited

U.S. PATENT DOCUMENTS

| | | | |
|---|---|---|---|
| 3,076,452 | 2/1963 | Rothe | 128/714 |
| 3,547,106 | 12/1970 | Bornmann | 128/721 |
| 4,619,270 | 10/1986 | Margolis et al. | 128/721 |
| 4,681,098 | 7/1987 | Lee | 128/670 |

OTHER PUBLICATIONS

"A Three Directional Ballistocardiograph", Nomura et al., Japanese Circulation Journal, vol. 30, Mar. 1966.
"The Ultra-Low-Frequency Ballistocardiogram in a Young California Gray Whale", Smith et al., Bibl. Cardiology, vol. 32 pp. 94–100.
Nyoboer et al., "Biaxial Servo Counterforce Ballistocardiograms in Man" Proc. 17th ann. Meet. Ballistocard. Res. Soc., Atlantic City 1973 Bibl. Cardiol. 34:68–72.
Calderale et al. "A New ULF-Bcg Bed: Two Degrees of Freedom, Air Bearings, Hyperboloidic Surface", Proc. 4th World Congr. Ballistocard. and Cardiovasc. Dynamics, Amsterdam 1975, Biblthca. Cardiol. 35:75–81.
H. Thal, "Uber eine Indirekte Methode zur Kontinuierlichen Atmungsregistrierung", Universitat Dusseldorf, 1973, pp. 5–10, 12, 15–20, 35.
J. E. Lewin, "An Apnoea-Alarm Mattress", The Lancet, Sep. 27, 1986 pp. 667–668.
A. M. Blake et al., "Clinical Assessment of Apnoea-Alarm Mattress for Newborn Infants", The Lancet, Jul. 25, 1970, pp. 183–185.
J. Gundersen et al., "Monitoring of Breathing with a Segmental Air-Filled Mattress", Medical & Biological Engineering, vol. 9, 1970, pp. 541–547.

Primary Examiner—Max Hindenburg
Assistant Examiner—Randy Citrin
Attorney, Agent, or Firm—Fleit, Jacobson, Cohn, Price, Holman & Stern

[57] ABSTRACT

An apparatus for monitoring respiration and cardiac activity of a person lying in a bed comprises a bed mounted for polydirectional movement and subjected to a restoring force when the bed is disturbed from its normal position. Pulses originiating from the person are detected by a vertically oriented sensor and a pair of horizontally oriented sensors thereby permitting monitoring of a wide range of respiratory and cardiac activity. In one arrangement, the bed is suspended by cords or on a vertical frame from a bracket. In other arrangements, the bed is variously mounted on a gimbal mechanism, on a support column which passes through a bearing ball, by flotation, and by a universal bearing joint.

1 Claim, 3 Drawing Sheets

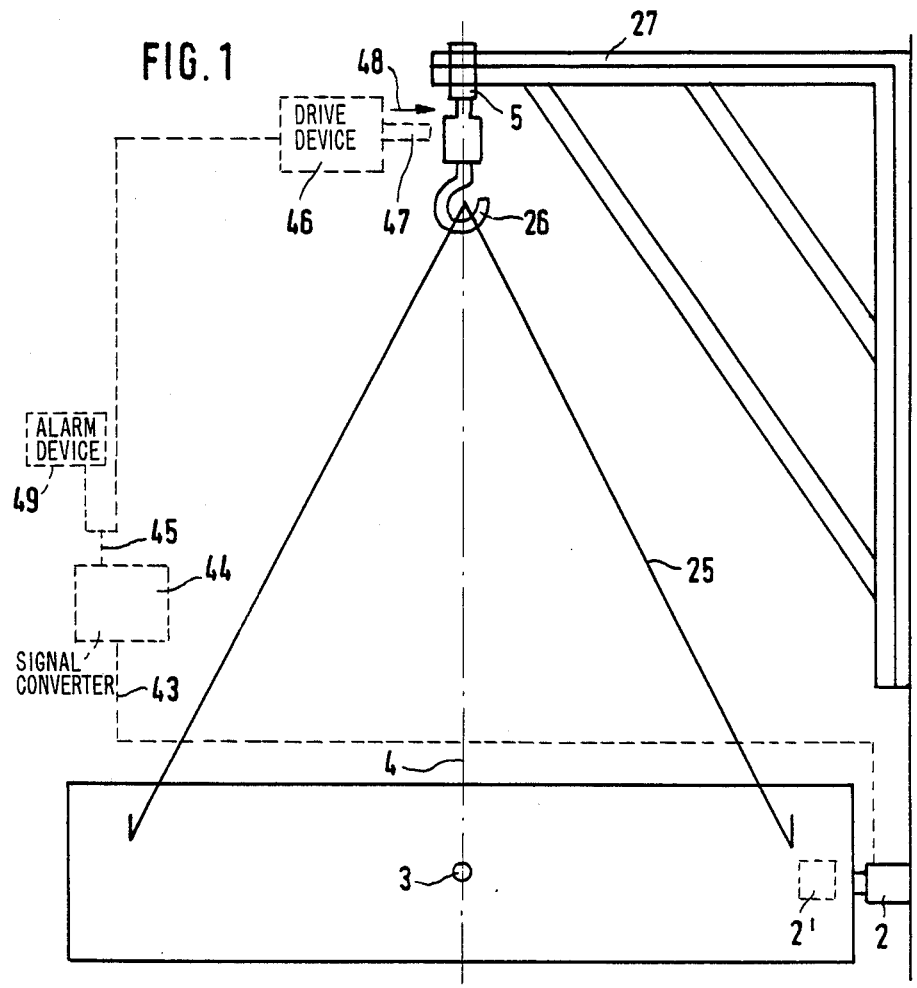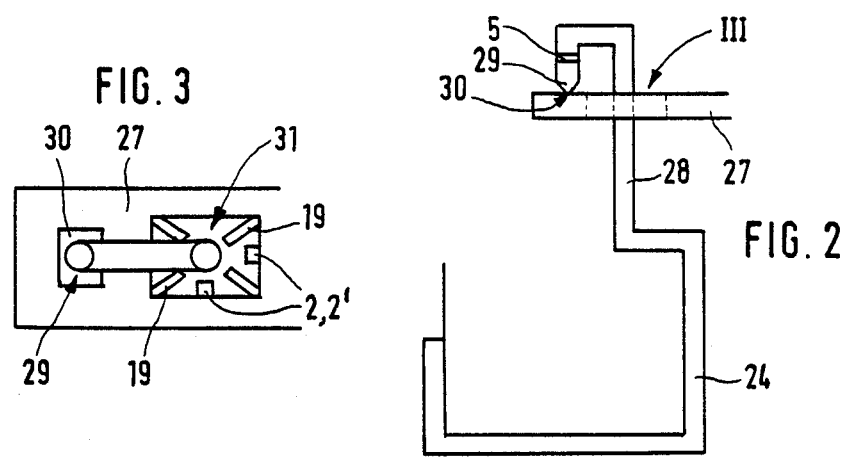

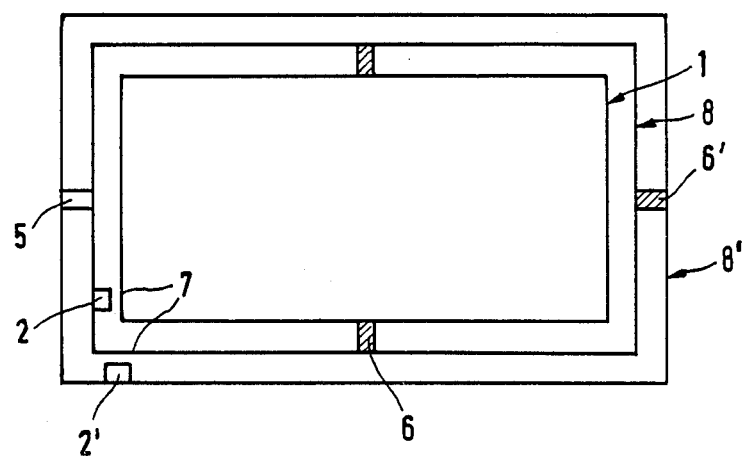
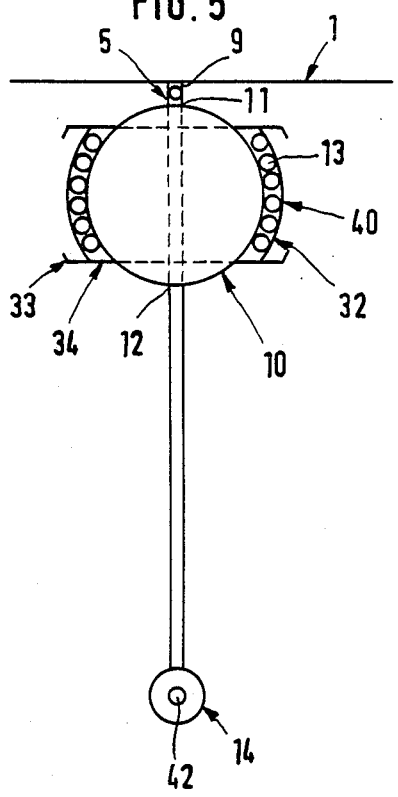
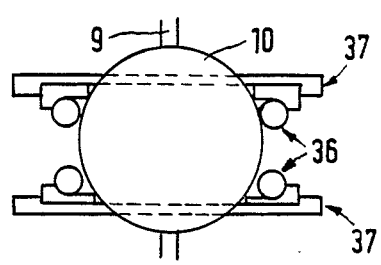
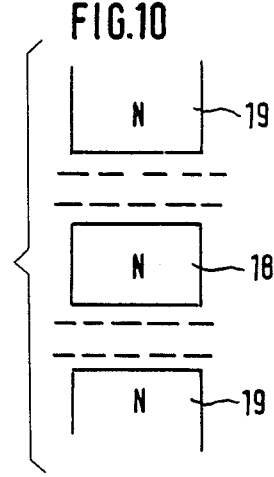

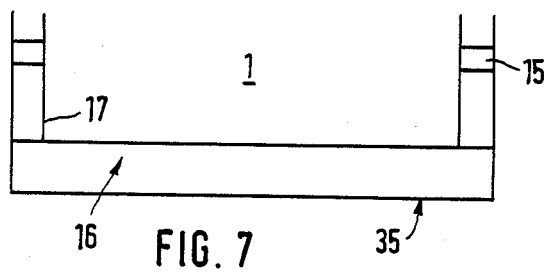
FIG. 7
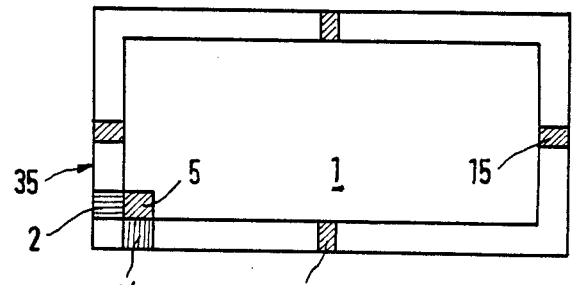
FIG. 8
FIG. 9
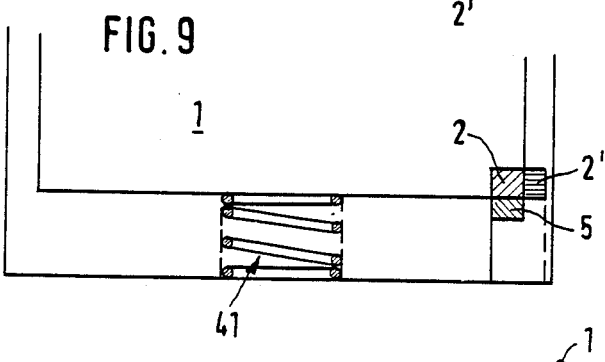
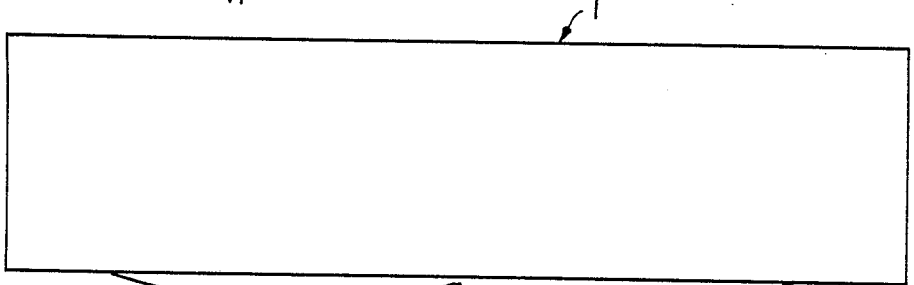
FIG. 11
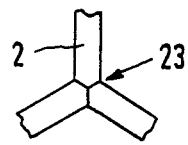
FIG. 12

4,884,578

APPARATUS FOR MONITORING RESPIRATION AND CARDIAC ACTIVITY

This is a division of application Ser. No. 917,429, filed Oct. 10, 1986, now abandoned.

BACKGROUND OF THE INVENTION

The invention relates to an apparatus for monitoring the respiration and cardiac activity of a person, especially but not exclusively a small child, lying in a bed, and which includes a sensor responsive to pulses originating from the person being monitored.

Such an apparatus is described in the paper "An indirect method for the continuous recording of respiration" by H. U. Thal, Dusseldorf University, 1973. According to this paper, piezoelectric load cells are built into the legs at the foot of the bed. The inhalation and exhalation of the patient results in a displacement of the center of gravity so that the feet of the bed are accordingly subjected to varying loads. These loads are converted to electrical signals by the load cells and these signals are amplified to produce output signals. In this manner, there are obtained simultaneously a so-called ballistocardiogram which, at a corresponding frequency, is characteristic of the cardiac activity, and a respiratory curve which, at a lower frequency, indicates respiratory activity. In this case, the signals originating from the cardiac activity are removed by means of a corresponding filter in order to obtain clear information about the course of respiration. This type of monitoring is of considerable importance not only in the intensive care unit of a hospital but also in a ward for new-born babies because in this manner, by appropriate use of the output signals, indications of respiratory arrest can be recognised immediately so that the necessary countermeasures can be taken. The advantage of this method is that it is possible to monitor respiratory activity without having to undertake any measurements on the actual patient or new-born baby. Further possibilities of monitoring on this basis are, however, neither anticipated nor possible.

In contrast, the problem underlying the invention is to obtain more extensive information about the respiratory and cardiac activity than is possible with this known apparatus. It is desirable therefore to have, at least in addition to information about respiratory activity, continuous information about cardiac activity on the basis of reliably usable signals. It is also desirable for the information to be extended in the direction of a more highly differentiated monitoring of both respiration and cardiac activity. In the case of respiration, additional details about the type of respiration (abdominal or chest respiration) and the respiration pressure are of interest, while in the case of cardiac activity the direction of blood circulation, especially in new-born children, deserves increased observation. For example, passage of blood through a still open *ductus arteriosus* would give a characteristically directed pulse. In connecting the pulmonary artery with the descending aorta, the *ductus arteriosus* forms an angle of less than 90°. Different pulse components would be produced depending on whether the patient was lying on his back or abdomen or on his right or left side.

SUMMARY OF THE INVENTION

It is an object of this invention to obtain more extensive information about respiratory and cardiac activity.

According to this invention, there is provided an apparatus for monitoring respiration and cardiac activity in a person lying in a bed, said apparatus comprising:

means for mounting the bed for polydirectional movement, said bed being subjected to a restoring force upon being disturbed from its normal position;

a first sensor oriented in a first direction and responsive to pulses originating from a person being monitored; and at least one further sensor oriented in a further direction and responsive to pulses originating from the person being monitored.

The invention makes it possible for the bed to react to a wider range of pulses than those recorded hitherto and which originate from weight displacement and consequent displacement of the center of gravity. In this context pulses are, in a general sense, short duration actions of mechanical amplitude or their short duration deviations from a base value. Consequently, directional information is obtained not only about the weight displacement during respiration but also about the associated course of the reaction force during inhalation and exhalation. Since the bed is not only mounted for polydirectional movement, but is also subject to a restoring force, the extent to which changes in the position of the bed actually occur is of less significance. For the examination of the processes to be recorded there is available at least one sensor oriented in a first direction and a further sensor oriented in a further direction so that at least two components of the pulses can form the basis of the evaluation. A further differentiation in the evaluation results from the fact that, in contrast to the prior art, the signals originating from the cardiac activity are no longer filtered out but are subject to simultaneous monitoring. To this extent the signal frequency and signal shape are of differential importance since they allow the pulses originating from respiratory activity and cardiac activity to be separated. Each of these processes involves the recording of at least two pulse components, these two components being oriented in two different directions. Advantageously, the first sensor is oriented in the vertical direction and said at least one further sensor is oriented in a horizontal direction. Especially advantageous is the orientation of two sensors in the horizontal direction which, for their part, are at right-angles to one another. Pulse components recorded in this manner have, together with their differentiation brought about by frequency, an extensive meaningfulness with regard to directional pulses of respiratory and cardiac activity.

The apparatus according to the invention can be designed in different ways. In order to ensure polydirectional movement a single device from which the bed is suspended is located above the center of gravity of the bed or alternatively support of the bed underneath its center of gravity may be considered. In the first case, the restoring moment in the case of deviations from the normal position is provided on the basis of the displacement of the center of gravity. In the second case, additional means are provided which make deviation from the normal position unstable and which bring about repositioning. As such additional means, which may operate without contact, there may be provided on the bed and at a fixed remote position, for example, magnets having the same polarity on the basis of which the bed can be maintained in a normal position. Alternatively, there may be used weights cooperating with the support itself by means of which the center of gravity of the entire system can be appropriately displaced thereby providing effective restoring forces. In addition to the first sensor, at least one further sensor is used in every case and it is merely a question of so arranging the sensors according to individual embodiments of the invention that they allow meaningful and differentiated signals.

Where the bed is suspended from a single device located above the center of gravity of the bed the first sensor is advantageously oriented in the direction of gravitational action of the center of gravity and said at least one further sensor is spaced horizontally from the direction of action to cooperate with the single suspension device or the bed when the bed is disturbed from its normal position.

The bed can also be mounted on a gimbal mechanism, in which case the first sensor is located at one of the supports of one of the shafts of the gimbal mechanism, while said at least one further sensor is oriented towards an edge of the bed or an edge of a frame which forms part of the gimbal mechanism. The last-mentioned arrangement has the advantage that the bed is freely accessible from above.

In an arrangement which provides a similar advantage, the mounting means comprises a bearing ball, a support column attached to the underside of the bed and passing through the bearing ball, and a set of balls which act as a mounting for the bearing ball. Advantageously, after passing through the bearing ball, the support column is provided with a counterweight. The first sensor can be arranged directly on the support column between the bearing ball and the bed while said at least one further sensor can be associated with the support column. Part of such a further sensor, for example, elements of a Hall-effect generator, a capacitor or beam-relecting or beam-producing means can be provided on the support column. The remaining part of such a further sensor is fixedly mounted, such remaining part being for example, a receiver that shows the extent of any deflection.

In another arrangement, the mounting means supports the bed by flotation. With this arrangement, the mounting means may also include a compression spring for supporting the bed at a central position thereof. The first sensor may be located at a horizontal edge of the bed and said at least one further sensor may be oriented towards a vertical edge of the bed. The mounting means may include magnetic poles directed outwardly from the sides of the bed and fixed magnets aligned with said poles so as to bias the bed into its normal position.

In an especially space-saving and effective arrangement the mounting means may comprise a universal ball joint provided on the base of the bed and directed downwardly therefrom, said universal ball joint being supported at a bearing point, and a weight located inside the universal ball joint is arranged so that the position of the common center of gravity of the bed, the universal ball joint and said weight is located so that the bed is biased towards its normal position. The first sensor is located in the vicinity of the bearing point of the ball joint on a fixed substrate and oriented with the bearing point. Said at least one further sensor may be oriented towards an edge of the bed. In addition to the ready accessibility of the bed from all sides, it is easy to provide an adequately heavy weight within the universal ball joint so that the desired displacement of the center of gravity of the entire system is achieved.

Where the first sensor is vertically oriented it is suitable also for static measurements, especially the weight of new-born babies.

BRIEF DESCRIPTION OF THE DRAWINGS

The invention is explained below with reference to the drawings relating to embodiments.

FIG. 1 shows a first arrangement of the bed and sensors,

FIG. 2 shows a modified embodiment of the arrangement according to FIG. 1,

FIG. 3 shows an enlarged section of region III of the embodiment according to FIG. 2, FIG. 4 shows a gimbal mechanism for mounting the bed with sensors attached, FIG. 5 shows an arrangement of the bed in which it is mounted by means of a bearing ball and the positions of the sensors, FIG. 6 shows a modification of the bearing ball according to FIG. 5, FIG. 7 shows a side view of an arrangement in which the bed is mounted by flotation, FIG. 8 shows a plan view of the arrangement according to FIG. 7, FIG. 9 shows a modified embodiment of the arrangement according to FIGS. 7 and 8, FIG. 10 shows a magnetic position-stabilising means, FIG. 11 shows an arrangement in which the bed is mounted by a universal ball joint, and FIG. 12 shows a position of horizontally oriented sensors for the arrangement according to FIG. 11.

DETAILED DESCRIPTION OF THE INVENTION

Referring now to FIG. 1, a bed 1 is suspended above its center of gravity 3 on a hook 26 of a rigid wall bracket 27 by means of center 25. In this suspension, a vertically oriented sensor 5 is located so that it lies in the direction of action 4 of the center of gravity 3 of the bed 1. In this manner, the forces exerted in the vertical direction are recorded.

The righthand sidewall of the bed 1 is supported by means of an intermediate support member at a stationary wall, and a horizontally oriented sensor 2 is mounted in this support member. There is also shown, by a broken line, a further horizontally oriented sensor 2' which permits the forces directed at an angle of 90° to the direction of the sensor 2 to be detected. As soon as the bed 1 is subject to any deviation from its normal position, it automatically returns to its normal position under the action of the moment exerted by the gravitational force at its center of gravity 3.

In this manner the arrangement according to FIG. 1 fulfills the essence of the invention in that on the one hand the vertical pulse component and on the other hand two horizontal pulse components at right-angles to one another are recorded. These pulses originate from the cardiac and respiratory actions of a person lying in the bed 1.

Instead of cords 25, the embodiment according to FIG. 2 uses a support frame 24 in which a vertical frame arm 28 is bent at right-angles toward the center of the bed so that a pivot point 29 is formed. The support frame 24 holds the bed 1 and is supported on the projecting wall bracket 27 by the pivot point 29 at a bearing point 30. The vertically oriented sensor 5 is mounted in the pivot point 29. The wall bracket 27 has, as shown in FIG. 3, a cut-away portion 31 in the walls of which are the horizontally oriented sensors 2, 2' which are oriented at an angle of 90° to the frame arm 28. By reflecting a sensor beam from the frame arm 28 towards, for example a camera having a linear array of photodiodes, deflections of the frame arm 28 from its normal position may be detected. In addition, the sensors can, insofar as they are integrated in components, be designed as resistors responsive to tensile or compressive strain. FIG. 3 also shows the bearing point 30 designed from the viewpoint of a stable mounting. It also shows the poles of fixed magnets 19 which are aligned with one another in such a manner that the frame arm 29 is stabilised in its normal position, which to this extent is an additional stabilising force effective in addition to the stabilisation on the basis of the position of the center of gravity.

A gimbal mechanism is shown in FIG. 4 and this includes two bearing shafts 6 and 6' arranged at right-angles to each other, the bearing shaft 6 mounting the bed 1 directly in a frame 8 which, for its part, is mounted in a fixed frame 8' by means of the bearing shaft 6'. Underneath a support for the bearing shaft 6' there is a sensor 5 oriented in the vertical direction, while two other sensors 2, 2' oriented horizontally on the edges 7, record on the one hand deviations of the frame 8 and on the other hand deviations of the bed 1.

In the arrangement of FIG. 5, the bed 1 is mounted by means of a support column 9 which passes through a bearing ball 10 at upper and lower penetration points 11 and 12. The bearing ball 10 is supported in a ball-bearing cage 40 by support balls 13. An outer ball shell 32 of the cage 40 is held by a support shell 33 which is provided with a seal 34 which permits rotation with respect to the bearing ball 10. The lower part of the support column 9 has a counter-weight 14 which is so arranged that it stabilises the normal position of the bed 1, the frictional resistance between the bearing ball 10 and the support balls 13 being readily overcome. Between the upper penetration point 11 of the support column 9 through the bearing ball 10 and the base of the bed 1 is arranged the verticaly oriented sensor 5. The counter-weight 14 supports a reflector 42 on which is detected a sensor beam from a light source (not shown in the drawing) so that deviations of the bed 1 can be detected by horizontally oriented sensors. In the modification according to FIG. 6, there is used only an upper and lower ball-bearing collar 36. These ball-bearing collars 36 are secured in a holding frame 37. The mounting according to FIGS. 5 and 6 therefore acts like a pendulumn which counterbalances the movements of the bed 1 out of its normal position. The stabilisation of position of the basis of the center of gravity allows a combination of this type of bearing with that of FIG. 1.

In FIG. 7, there is shown an arrangement in which the bed is mounted by flotation. In this arrangement there is provided an outer shell 35 which, for example, accommodates a liquid. The base of the bed 1 in this case has a seal. The frame of the bed 1 is held at a distance with respect to the shell 35, this being the purpose of the supports 15. They are shown only diagrammatically in FIGS. 7 and 8. They can, similarly to the diagram of FIG. 3, be formed magnetically. For example, as shown in FIG. 10, magnetic poles 18 are arranged on the bed 1 while fixed magnets 19 are arranged to act in the same direction so that their poles attempt to maintain the poles 18 at a distance. As can be seen in FIG. 8, vertically oriented sensors 5 can be attached between the base of the bed 1 and the bearing shell 35, while horizontally oriented sensors 2, 2' are so arranged that they point towards the vertical edges 17 of the bed 1 and can accordingly detect any changes in position.

FIG. 9 shows a similar arrangement but in which the bed 1 is arranged on a spiral pressure spring 41. There can be seen again the vertically oriented sensor 5 and the two horizontally oriented sensors 2 and 2'.

In the arrangement according to FIG. 11, the bed 1 is arranged on a curved point-contact bearing 20, there being a heavy weight 21 between the base of the bed 1 and the curved point-contact bearing 20 so that the common center of gravity of the bed 1, cruved point-contact bearing 20 and weight 21 is located at 22 between the bed 1 and the weight 21 thereby stabilising the bed in its initial or normal position. As the weight of the curved point-contact bearing 20 is also taken into consideration in the common center of gravity, the curved point-contact bearing 20 is advantageously manufactured from a heavy material. The curved point-contact bearing 20 is supported at a bearing point 23 either on a horiziontal base 38 or on a bearing element 39 curved in the opposite direction. There is provided near the bearing point 23 the vertically oriented sensor 5 (not shown in this case). The sensor 5 is oriented in the direction of gravitational action of the common center of gravity at 22. The horizontally oriented sensors are oriented on the edges of the bed 1. FIG. 12 shows a further arrangement of sensors 2 which are mounted horizontally on the bearing point 23 so that they are arranged at an angle of 120° to each other. Deviations of the bed 1 in one or the other direction result in loading of the sensors 2, so that the signals originating therefrom are characteristic for the individual pulse component.

An arrangement of the weight 21 can be made according to its size and position and additionally from the viewpoint that thereby the natural oscillation of the entire arrangement is altered. In this manner unwanted oscillations of the entire arrangement can be avoided in that they occur at a frequency that does not result in any distortion of the respiratory or cardiac signals to be measured. To this extent, arrangement of the weight 21 improves the availability of reliably usable signals.

As known from the prior art, a sensor may supply its signals to a circuit which generates a secondary signal, in the absence of signals from the sensor. An alarm device is actuated by the secondary signal and this allows the nursing staff to take immediate countermeasures, for example, in the case of respiratory arrest. The present invention uses the secondary signal which actuates an alarm to additionally actuate an automatic waking device. For this purpose the secondary signal mentioned is used to switch on a drive device which imparts motion to the bed so that, in particular, small children are awakened thereby and begin to breath normally again. Even if the normalization of respiratory activity is not achieved completely thereby, valuable time is used until the nursing staff arrive following the simultaneous actuation of the alarm. The arrangement can also be so designed that the drive device causes only one single movement of the bed. In this case, the pulses originating from the person lying in the bed are not subject to interference by operation of the device.

The above-described arrangement is shown in FIG. 1 by the additional elements shown by the broken lines. Accordingly, a signal 43 passes from the sensor 2 to an amplifier and signal converter 44. The latter, shown here merely as a component in the form of a block diagram, is known in this form from the prior art. In the absence of the signal 43 for a predetermined time it produces a secondary signal 45. This secondary signal triggers according to the known prior art an alarm device 49. In the present invention there is additionally a parallel connection of the secondary signal to a drive device 46, for example an electric motor, so that when there is a signal 45 this drive device 46 is switched on. The drive device is constructed in such a manner that when the drive device 46 is on, a ram 47 can travel in the direction of the arrow 48. The ram 47 engages a component associated with the hook 26 and suspended on the wall bracket 27 so that the bed 1 is set in motion. This movement may already be sufficient to cause wakening and to remedy the temporary respiratory arrest.

I claim:

1. An apparatus for monitoring respiration and cardiac activity of a patient, comprising:

bed means for supporting thereon a patient to be monitored, the bed means having a base and an edge;

mounting means for mounting the bed means for polydirectional movement about a initial position thereof, the mounting means comprising a curved point-contact bearing provided on the base of the bed means and directed downwardly therefrom, said curved point-contact bearing being supported at a bearing point thereof by support means;

restoring means for restoring the bed means to said initial position, the restoring means comprising a weight provided inside the curved point-contact bearing and arranged such that the position of a common center of gravity of the bed means, the curved point-contact bearing and said weight is located for biasing the bed means towards said initial position when disturbed therefrom;

first sensor means located proximate said curved point-contact bearing bearing point and oriented in a first direction for sensing movement of the bed means in said first direction caused by heartbeat and respiration pulses originating from a patient being monitored; and at least one second sensor means provided on said bed means and oriented towards the edge of the bed means in a second direction different from said first direction for sensing movement of the bed means in said second direction caused by heartbeat and respiration pulses originating from a patient being monitored.

* * * * *